(12) United States Patent
Scarth et al.

(10) Patent No.: US 8,369,929 B2
(45) Date of Patent: Feb. 5, 2013

(54) PATIENT SUPPORT TABLE FOR USE IN MAGNETIC RESONACE IMAGING

(75) Inventors: Gordon Scarth, Winnipeg (CA); Alexander Shvartsberg, Winnipeg (CA); Franjo Vugrin, Winnipeg (CA); Wybrandus T. Schellekens, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 1029 days.

(21) Appl. No.: 12/333,032

(22) Filed: Dec. 11, 2008

(65) Prior Publication Data

US 2009/0306495 A1 Dec. 10, 2009

Related U.S. Application Data

(60) Provisional application No. 61/058,657, filed on Jun. 4, 2008.

(51) Int. Cl.
*A61B 5/055* (2006.01)
(52) U.S. Cl. .................. 600/415; 600/407; 600/410
(58) Field of Classification Search .................. 600/415; 5/601
See application file for complete search history.

(56) References Cited

U.S. PATENT DOCUMENTS

| | | |
|---|---|---|
| 4,595,899 A | 6/1986 | Smith |
| 5,007,425 A | 4/1991 | Vanek et al. |
| 5,099,846 A | 3/1992 | Hardy |
| 5,291,890 A | 3/1994 | Cline |
| 5,713,357 A | 2/1998 | Meulenbrugge |
| 5,735,278 A | 4/1998 | Hoult et al. |
| 5,788,624 A * | 8/1998 | Lu et al. ............................ 600/9 |
| 6,037,773 A * | 3/2000 | Mitsumata et al. ........... 324/318 |
| 6,101,239 A | 8/2000 | Kawasaki |
| 6,385,480 B1 | 5/2002 | Bachus |
| 6,754,519 B1 | 6/2004 | Hefetz |
| 6,812,700 B2 | 11/2004 | Fahrig |
| 6,934,574 B1 * | 8/2005 | Damadian et al. ............ 600/415 |
| 6,961,606 B2 | 11/2005 | DeSilits |
| 6,975,895 B1 | 12/2005 | Pelc |
| 2004/0143177 A1 | 7/2004 | Falbo, Sr. et al. |
| 2005/0187459 A1* | 8/2005 | Trequattrini et al. ......... 600/415 |
| 2005/0228267 A1 | 10/2005 | Bulkes et al. |
| 2006/0239524 A1 | 10/2006 | Desh |
| 2007/0016003 A1* | 1/2007 | Piron et al. .................... 600/415 |

FOREIGN PATENT DOCUMENTS

| | | |
|---|---|---|
| DE | 3931854 | 4/1991 |
| JP | 4183446 | 6/1992 |
| JP | 5344964 | 12/1993 |
| WO | WO2007147233 A1 | 12/2007 |

\* cited by examiner

*Primary Examiner* — Peter Luong
(74) *Attorney, Agent, or Firm* — Adrian D. Battison; Ade & Company Inc.

(57) ABSTRACT

A patient table for a common imaging system including Magnetic Resonance and X-ray retains the patient stationary in position prior to, during and subsequent to the imaging and includes a base, a patient support portion cantilevered from the base and a mattress. The RF posterior coil portions for the head and for the chest can be inserted into and removed from an operating position underneath the head and chest of the patient while patient remains supported. The chest coil is inserted from one edge in a cavity in the mattress which is reinforced by a sleeve. The signal communication cable from the chest coil is routed in front of the mattress and over the mattress so as to not to be exposed at the sides. The head coil is carried on a base plate of the patient support alongside the head support which remains in place.

25 Claims, 7 Drawing Sheets

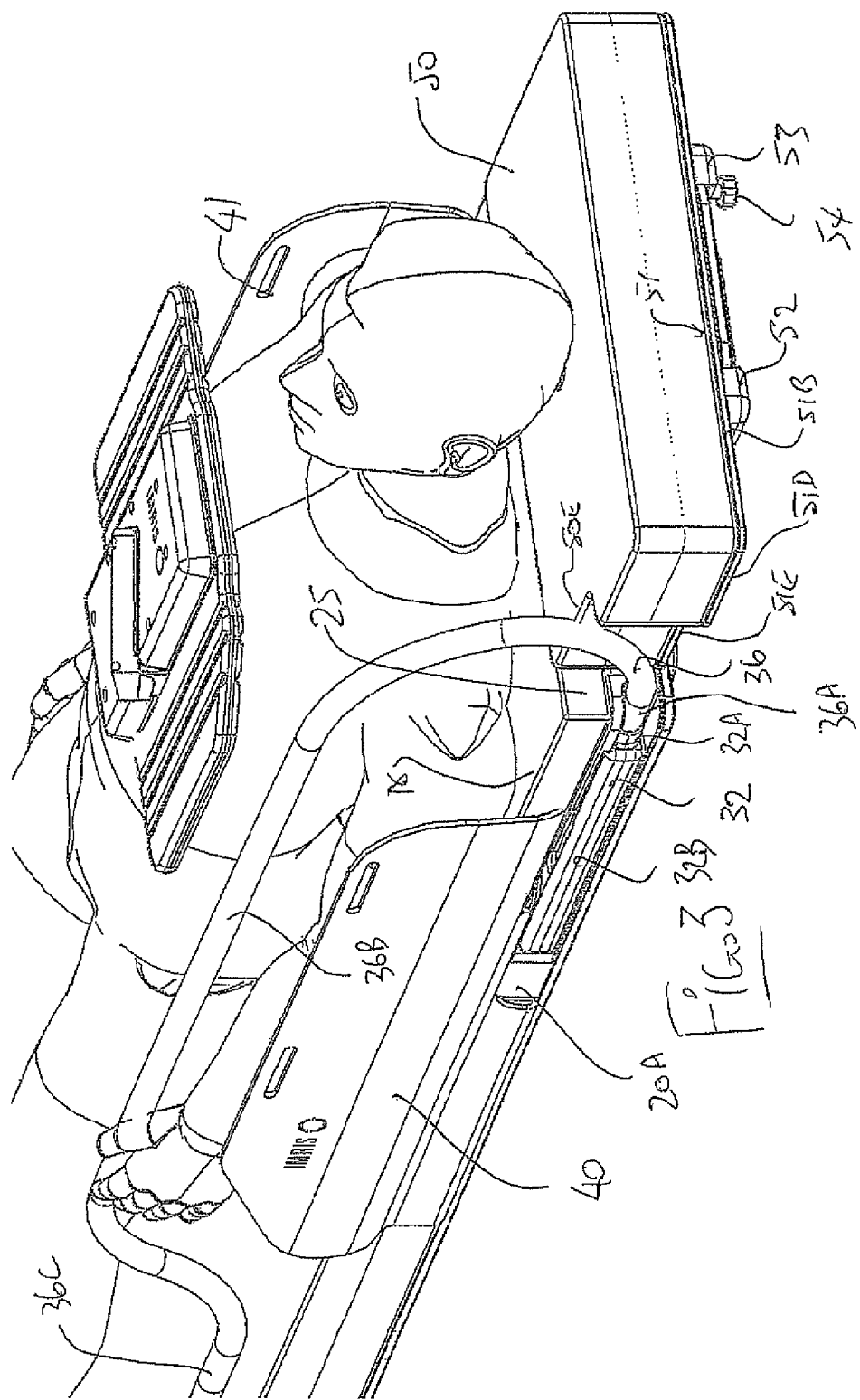

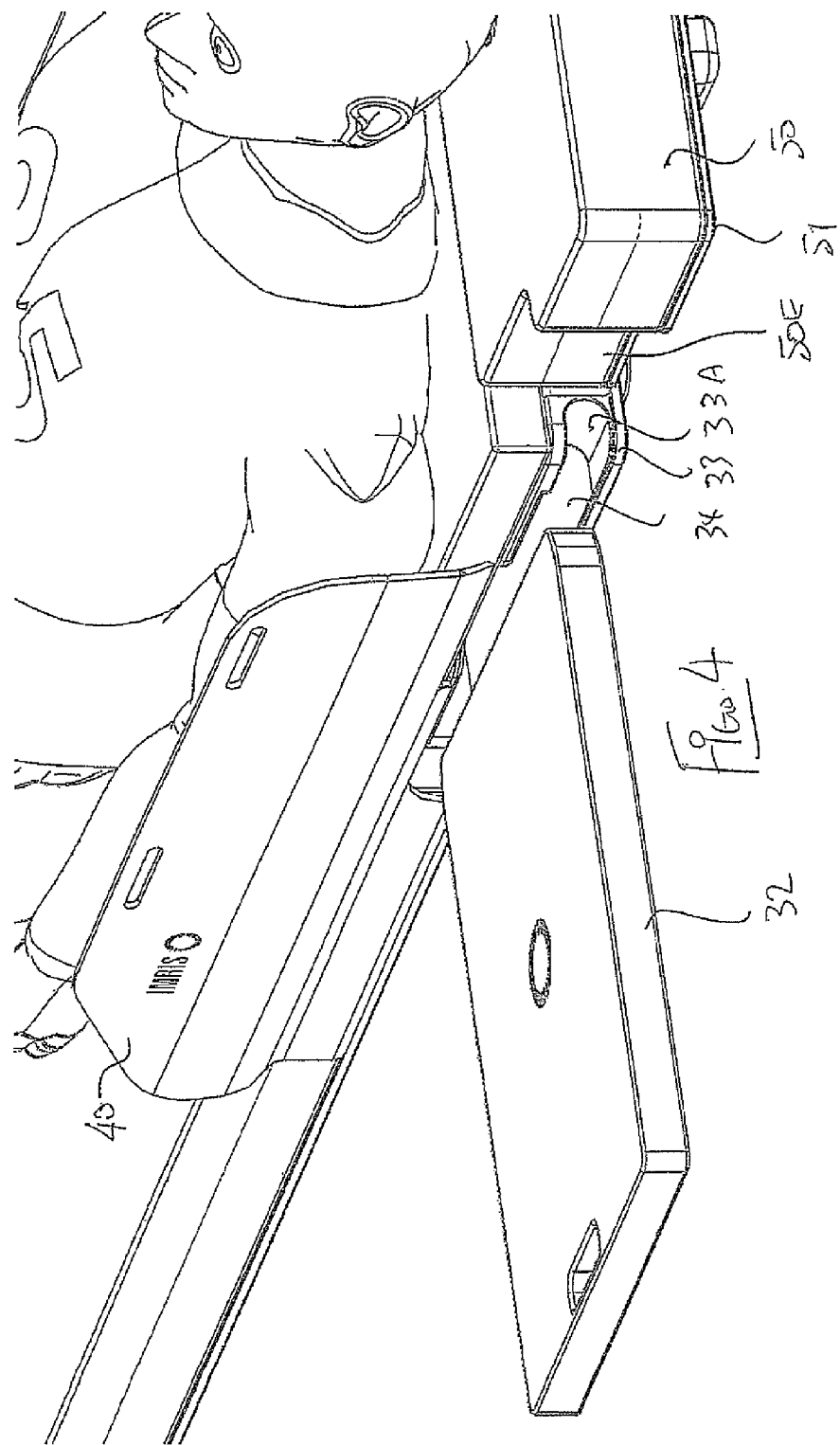

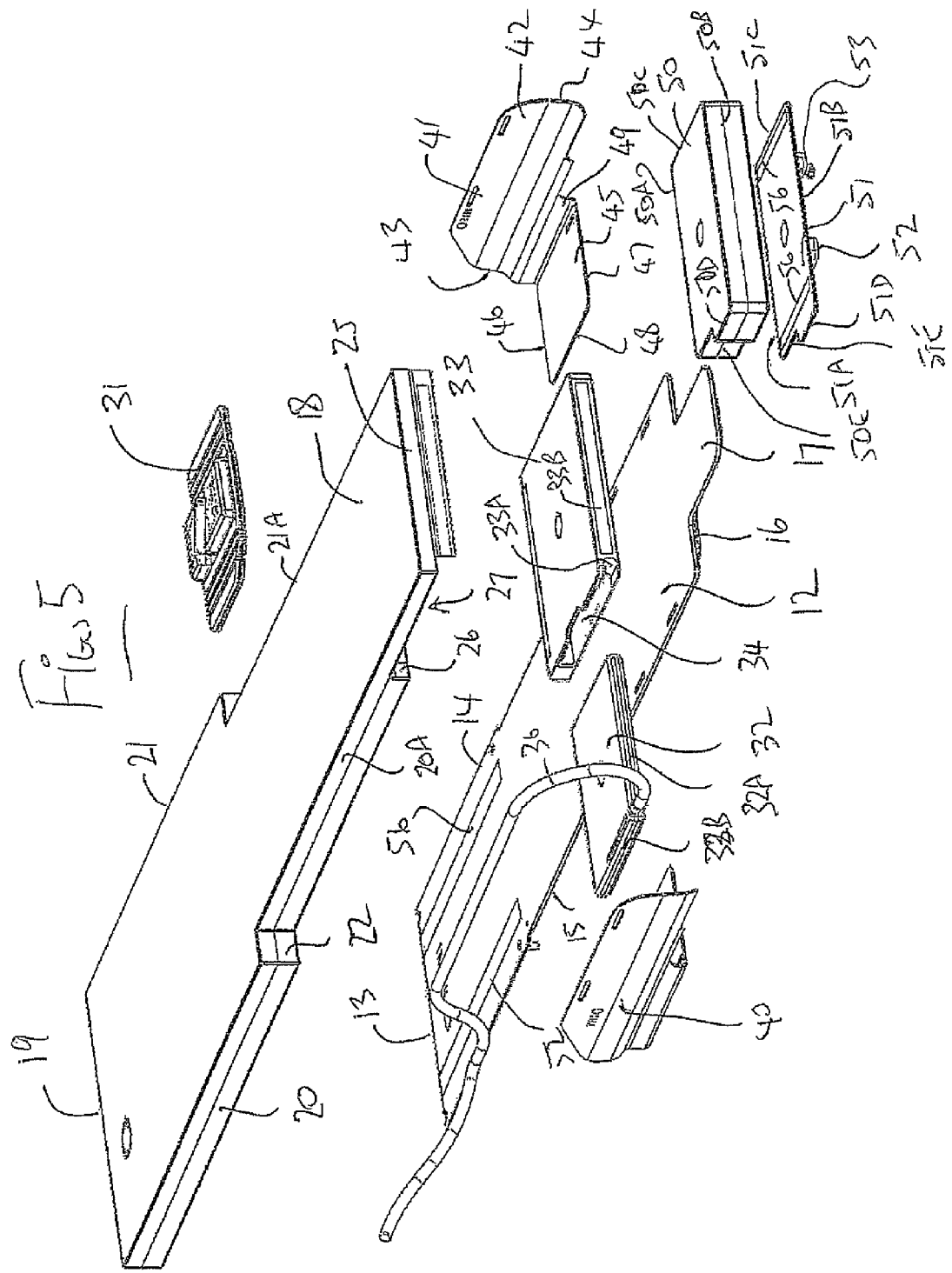

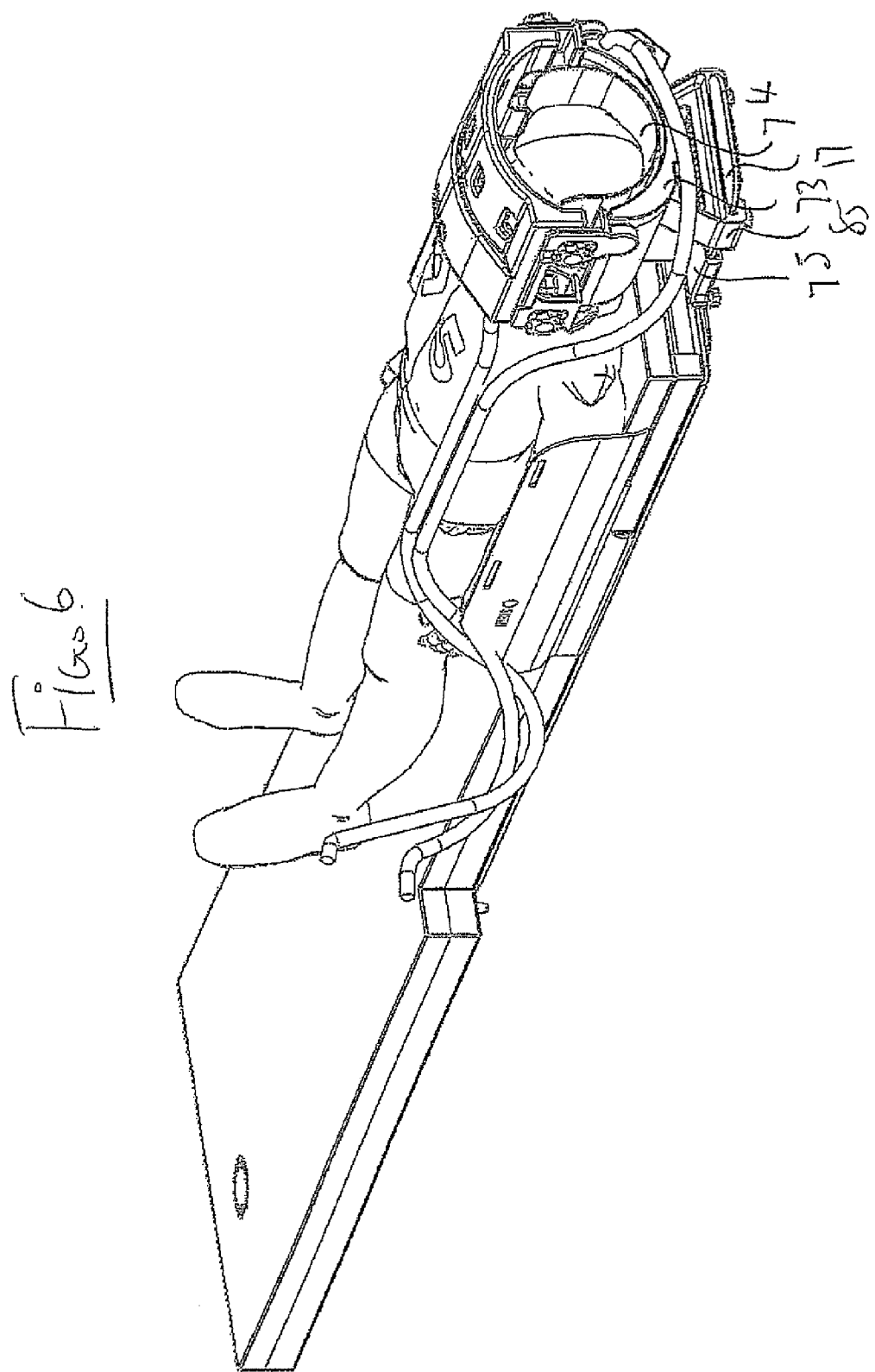

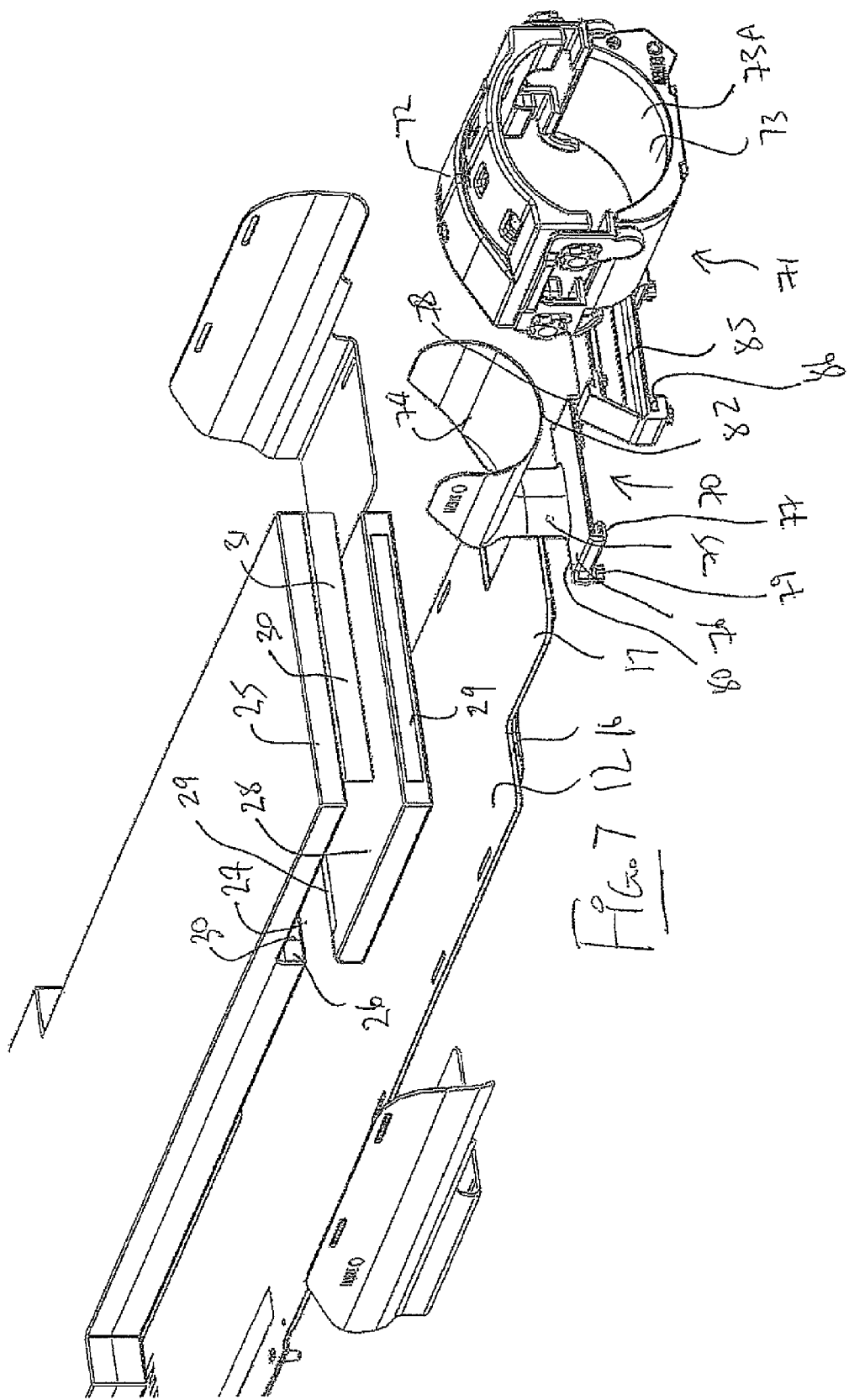

US 8,369,929 B2

PATIENT SUPPORT TABLE FOR USE IN MAGNETIC RESONACE IMAGING

This application claims the benefit under 35 U.S.C. 119 of Provisional Application No. 61/058,657 filed Jun. 4, 2008.

This invention relates to a patient support table for use in magnetic resonance imaging which can be used for example in an apparatus for obtaining Magnetic Resonance and X-Ray images of a patient.

BACKGROUND OF THE INVENTION

With MRI, a high field magnet, typically superconducting, is arranged in a torus configuration (like a donut) and with the patient lying down inside the magnet on a table where the magnetic field allows a pulsed and sequenced magnetic and EM field to probe the body to produce images, which allow the trained radiologist to determine with high probability the anatomy of the patient. MRI is sometimes performed using contrast agents introduced to the patient to provide even better contrast between different tissue types. MRI techniques are very good at detecting the anatomical location of different diseases, for example, tumours.

In U.S. Pat. No. 5,735,278 (Hoult et al) issued Apr. 7, 1998, disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients.

In Published PCT Application WO07147233A1 of the present Applicants published Dec. 27, 2007 and entitled ROTATABLE INTEGRATED SCANNER FOR DIAGNOSTIC AND SURGICAL IMAGING APPLICATIONS is disclosed an improvement to the above patent in which an additional rotational movement of the magnet is allowed.

A scanning system is known in which the patient is moved from an X-ray imaging system to an MR imaging system by transferring the patient from one imaging system to the other, for example, on a moveable table. The MR scanner is used to provide information complementary to that obtained using X-ray. It can be used, for example, to perform a baseline assessment prior to intervention as well as to perform a post-intervention assessment. Such an assessment may include perfusion and viability studies of the heart or of the brain.

U.S. Pat. No. 5,713,357 (Meulenbrugge) issued Feb. 3, 1998 and related U.S. Pat. No. 5,807,254 both of Phillips shows a combination of an X-ray system and an MRI system. The system is not for intra-operative uses and the magnet is not a cylinder. The magnet is not moved. The X-ray is moved side to side in FIG. 2. The patient is moved in FIG. 1.

U.S. Pat. No. 6,101,239 (Kawasaki) issued Aug. 8, 2000 to Hitachi provides an X ray and MRI operating simultaneously at the same location and methods to operate them in a timed manner to avoid interference. However this arrangement is not suitable for interventions by the medical team since the presence of the machines restricts access to the patient.

U.S. Pat. No. 6,385,480 (Bachus) issued May 7, 2002 of Siemens discloses what they call an angio-MR system where the radiographic angio-system cooperates with the MR system. There is provided a moving patient table which transfers the patient from the X-ray system at one location to the MRI at a second location.

US Patent Application 2006/0239524 (Desh) published October 26, 2006 of Siemens relates to diagnosis and treatment of cardiac diseases using MRI and X-ray. This is directed to a method of combining the images to analyze the diagnosis.

U.S. Pat. No. 6,975,895 (Pelc) issued Dec. 13, 2005 to Leland Stanford University provides a modified X ray tube for use in magnetic fields of an MRI system.

U.S. Pat. No. 6,812,700 (Fahrig) issued Nov. 2, 2004 of Leland Stanford University discloses a related system in which the perturbations in the magnetic field of the MRI caused by the X-ray system are compensated.

U.S. Pat. No. 4,595,899 (Smith) issued Jun. 17, 1986 to Leland Stanford University provides an MRI system.

U.S. Pat. No. 5,099,846 (Hardy) issued Mar. 31, 1992 relates to combining images from different imaging modalities and is primarily about the software for combining the images such as X-ray and NMR.

U.S. Pat. No. 6,754,519 (Hefetz) issued Jun. 22, 2004 to Elgems discloses two imaging systems such as CT and MRI where the two systems are mounted on a common rail system for rolling movement from a common position to a spaced position.

U.S. Pat. No. 5,291,890 (Cline) issued Mar. 8, 1994 to GE discloses a patient heat treatment system where the heat is detected using an MRI.

U.S. Pat. No. 6,961,606 (DeSilits) issued Nov. 1, 2005 to Phillips discloses two imaging systems such as CT and PET where the two systems are mounted on a common rail system for rolling movement from a common position together for common scanning of the patient to a spaced apart position.

German patent application 39 31 854 of Muller published Apr. 4, 1991 discloses an NMR apparatus using a laser coagulation stereotactic system.

Japanese application 05344964 of Toshiba shows a combination of an X-ray system and an MRI system. This is application is filed only in Japan and provides what is apparently a crude system.

Japanese patent application 4183446 published Jun. 30, 1992 by Res Dev Corp of Japan discloses the use of MRI and X-Ray in a common apparatus.

One element which must be designed for use with a combined imaging system of the type described above is that of the patient support table.

SUMMARY OF THE INVENTION

It is one object of the present invention to provide a patient support table which can be used in a combined imaging system of the type described above.

It is a further object of the present invention to provide a patient support table which allows imaging of the chest area.

It is a further object of the present invention to provide a patient support table which allows imaging of the head, neck and upper C-spine areas.

It is a further object of the present invention to provide a patient support table which allows the posterior coil portion of the RF coil to be inserted and removed while the patient remains supported and without moving the patient.

It is a further object of the present invention to provide a patient support table which allows the table to be used in the high magnetic field of an MRI magnet.

It is a further object of the present invention to provide a patient support table which allows the arms of the patient to be located on the table while avoiding interfering with imaging of the chest area.

It is a further object of the present invention to provide a patient support table which allows an effective routing of the cables of MR coils, for example, cardiac or neuro coils, so as not to interfere with the introduction of the table and patient into the MRI magnet.

According to a first aspect of the invention there is provided an apparatus for use in Magnetic Resonance imaging of a part of a patient comprising:

patient support table;

an RF coil for use in the MR imaging including a posterior coil portion for location underneath the patient;

the patent support table comprising a table support base for mounting in a fixed position in an imaging suite;

the patent support table comprising an upper patient support portion for structurally supporting the patient with the part of the patient exposed for imaging;

the upper patient support portion of the patient support table being cantilevered from the table support base in a longitudinal direction so as to extend into a bore of an MRI magnet from one end of the magnet to an imaging zone of the magnet;

a mattress applied over the patient support portion;

the upper patient support portion and the mattress being arranged such that the patient is fully supported prior to, during and subsequent to the imaging;

the posterior RF coil portion being arranged relative to the patient support and the mattress such that the posterior coil portion can be inserted into an operating position underneath the part of the patient to be imaged and removed from the operating position while patient remains fully supported and no movement of the patient is required.

Preferably there is provided a receptacle for the posterior RF coil in one or both of the patient support portion and the mattress portion.

Preferably the receptacle is provided in the mattress but it can be in the patient support portion of the table or it can be provided as a part of both the mattress and the support portion.

Preferably the head and upper torso of the patient both remain fully supported prior to, during and subsequent to the imaging.

According to a second aspect of the invention there is provided an apparatus for use in Magnetic Resonance imaging of a part of a patient comprising:

patient support table;

an RF coil for use in the MR imaging of the upper part of the torso of the patient including a posterior coil portion for location underneath the part a;

the patent support table comprising a table support base for mounting in fixed position in an imaging suite;

the patent support table comprising an upper patient support portion for structurally supporting the patient with the part of the patient exposed for imaging;

the upper patient support portion of the patient support table being cantilevered from the table support base in a longitudinal direction so as to extend into a bore of an MRI magnet from one end of the magnet to an imaging zone of the magnet;

a mattress applied over the patient support portion having an upper surface for contacting the patient;

a receptacle in one or both of the patient support portion and the mattress for receiving the posterior coil portion;

the receptacle having an inlet opening located and arranged such that, with the mattress in place on the support portion and the patient in place on the mattress, the opening is exposed beneath the upper surface.

Preferably the receptacle is provided in the mattress.

Preferably the opening is in an edge such that the coil in a flat panel form is inserted into the receptacle through the opening by movement in a horizontal direction.

Preferably the opening is in one side edge bit it could be at a front edge of the table underneath the head support.

Preferably there is provided a stiffener sleeve for location in the receptacle in the mattress into which sleeve the posterior coil portion is inserted, the stiffener sleeve providing support for the patient with the posterior coil portion removed.

Preferably there is provided a replacement insert portion for insertion into the receptacle in the mattress when the posterior coil portion is not used.

Preferably the receptacle extends substantially across the full width of the mattress.

Preferably the receptacle extends partly through the thickness of the mattress with a portion of the thickness of the mattress above the receptacle.

Preferably the receptacle is located at a forward end of the mattress.

According to a third aspect of the invention there is provided an apparatus for use in Magnetic Resonance imaging of a part of a patient comprising:

patient support table;

an RF coil for use in the MR imaging of the head of the patient including a posterior coil portion for location underneath the head;

the patent support table comprising a table support base for mounting in fixed position in an imaging suite;

the patent support table comprising an upper patient support portion for structurally supporting the patient with the part of the patient exposed for imaging;

the upper patient support portion of the patient support table being cantilevered from the table support base in a longitudinal direction so as to extend into a bore of an MRI magnet from one end of the magnet to an imaging zone of the magnet;

a mattress applied over the patient support portion having an upper surface for contacting the patient;

a head support member connected to the table and defining an upper support surface for engaging and supporting the head of the patient;

the posterior coil portion being shaped and arranged to be inserted into and removed from an operating position underneath the upper support surface of the head support member.

Preferably the head support member comprises a channel portion having an upper channel shaped surface for cupping around the rear of the head of the patient a lower channel shaped surface and the posterior coil portion includes a channel shaped inner surface for location closely underneath the lower channel shaped surface of the channel portion.

Preferably the channel portion is cantilevered from a connection member at the patient support portion of the table.

Preferably the connection member is removable from the patient support portion of the table.

Preferably the patient support portion of the table includes an outwardly projecting end portion and wherein the connection member includes a clamping portion for sliding engagement onto an end of the end portion.

Preferably the posterior coil portion includes a clamping portion for sliding engagement onto an end of the end portion alongside the clamping portion of the connection member.

Preferably there is provided a head support plate and mattress portion therefor for use with the head support member removed, which head support plate includes a clamping portion for sliding engagement onto an end of the end portion.

According to a fourth aspect of the invention there is provided an apparatus patient support table for use in magnetic resonance imaging of a part of a patient comprising:

a table support base for mounting in fixed position in an imaging suite and an upper patient support portion on which the patient can lie with the part of the patient exposed for imaging;

the upper patient support portion of the patient support table being cantilevered from the table support base in a direction longitudinal of the axis so as to extend into a bore of an MRI magnet from one end of the magnet to an imaging zone of the magnet;

a mattress applied over the patient support portion;

wherein the patient support portion is formed from a plastics material reinforced by reinforcing fiber where the reinforcing fibers are non-conductive.

Preferably the reinforcing contains no carbon fibers.

According to a fifth aspect of the invention there is provided a patient support table for use in imaging of the upper part of the torso of a patient comprising;

a table support base for mounting in fixed position in an imaging suite and an upper patient support portion on which the patient can lie with the part of the patient exposed for imaging;

the upper patient support portion of the patient support table being cantilevered from the table support base in a direction longitudinal of the axis so as to extend into a bore of an MRI magnet from one end of the magnet to an imaging zone of the magnet;

a mattress applied over the patient support portion;

a pair of arm engagement members each arranged on a respective side of the patient support portion for engaging and retaining a respective one of the arms of the patient on the mattress while the patient lies prone on the mattress;

each arm engagement member comprising an elongate plate portion arranged to extend along the side of the mattress and to stand upwardly therefrom to hold the arm of the patient inwardly with a rearward most edge adjacent the hand of the patient and a forwardmost edge adjacent the shoulder of the patient;

each arm engagement member comprising a mounting plate connected to the elongate plate portion and arranged to extend generally at right angles to the elongate plate portion between the mattress and the patient support portion of the table for holding the arm engagement position in place at the side of the patient support portion of the table;

wherein the mounting plate has a forwardmost edge spaced rearwardly from the forwardmost edge of the elongate plate portion and located such that the mounting plate is wholly located on the patient support portion of the table at a position spaced from the upper torso of the patient.

Preferably the mounting plate is connected to a vertical portion connected thereto and extending upwardly to the elongate plate portion to hold the elongate plate portion at a raised position from the mounting plate, the vertical portion having a forwardmost edge coterminous with the mounting plate.

Preferably there is provided a receptacle in one or both of the patient support portion and the mattress for receiving a posterior coil portion of an RF coil for location underneath the patient for use in the MR imaging and wherein the mounting plate is arranged such that the forwardmost edge thereof is spaced in the rearward direction from the receptacle.

Preferably the receptacle is provided in the mattress.

Preferably an opening into the receptacle is in one side edge of the mattress such that the coil is inserted into the receptacle through the opening by movement in a horizontal direction.

According to a sixth aspect of the invention there is provided an apparatus for use in Magnetic Resonance imaging of a part of a patient comprising:

patient support table;

an RF coil for use in the MR imaging including a posterior coil portion for location underneath the patient and an anterior coil portion for location on top of the patient;

the patent support table comprising a table support base for mounting in fixed position in an imaging suite;

the patent support table comprising an upper patient support portion for structurally supporting the patient with the part of the patient exposed for imaging;

the upper patient support portion of the patient support table being cantilevered from the table support base in a longitudinal direction so as to extend into a bore of an MRI magnet from one end of the magnet to an imaging zone of the magnet;

a mattress applied over the patient support portion;

the mattress having one side edge along one side of the patient support portion;

the posterior coil portion being located underneath the mattress;

the posterior coil portion including a cable for communication of RF signals from the posterior coil portion to a control system for controlling the magnetic resonance imaging with the cable being located at said one side edge;

the cable being connected to the posterior coil portion adjacent said one side edge but located such that the cable emerges from the posterior coil portion at an edge of the mattress recessed from said one side edge and passes from the posterior coil portion over the mattress without projecting outwardly beyond said one side edge.

Preferably the cable is connected to the posterior coil portion at a forward end thereof and is arranged such that the cable emerges from the posterior coil portion at a forwardmost edge of the mattress immediately adjacent said one side edge.

BRIEF DESCRIPTION OF THE DRAWINGS

FIG. 3 is an isometric view on an enlarged scale of a portion of the table of FIG. 2 and showing an insert portion for insertion into the receptacle in the mattress when the posterior coil portion is removed.

FIG. 4 is an isometric view on an enlarged scale of a portion of the table of FIG. 2.

FIG. 5 is an exploded view of the table of FIG. 2.

FIG. 6 is an isometric view of a table for mounting the patient, the base being omitted for convenience of illustration, and showing the RF coil construction for imaging of the head of the patient.

FIG. 7 is an exploded view of the table of FIG. 6.

DETAILED DESCRIPTION

Reference may be made to the abovementioned Published PCT Application WO07147233A1 of the present Applicants published Dec. 27, 2007 and entitled ROTATABLE INTEGRATED SCANNER FOR DIAGNOSTIC AND SURGI- CAL IMAGING APPLICATIONS in which is disclosed details of the construction of an MRI magnet suitable for use in the present arrangement. The disclosure of this document is incorporated herein by reference.

Figure 1:
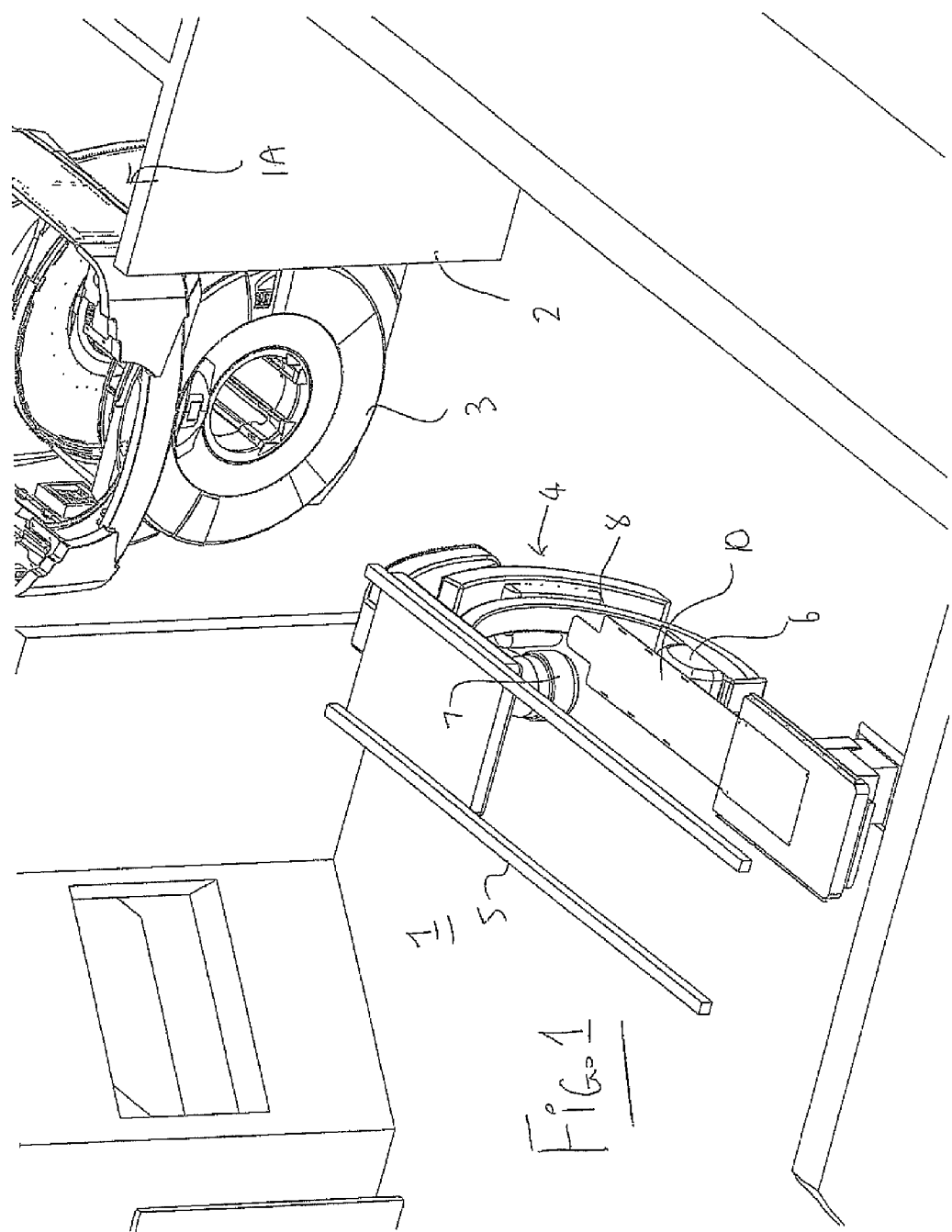
FIG. 1 is an isometric view of an Angiography room showing a patient table, an MRI magnet movable into a position for imaging the patient on the table and an arrangement for moving an X-Ray system.
Figure 2:
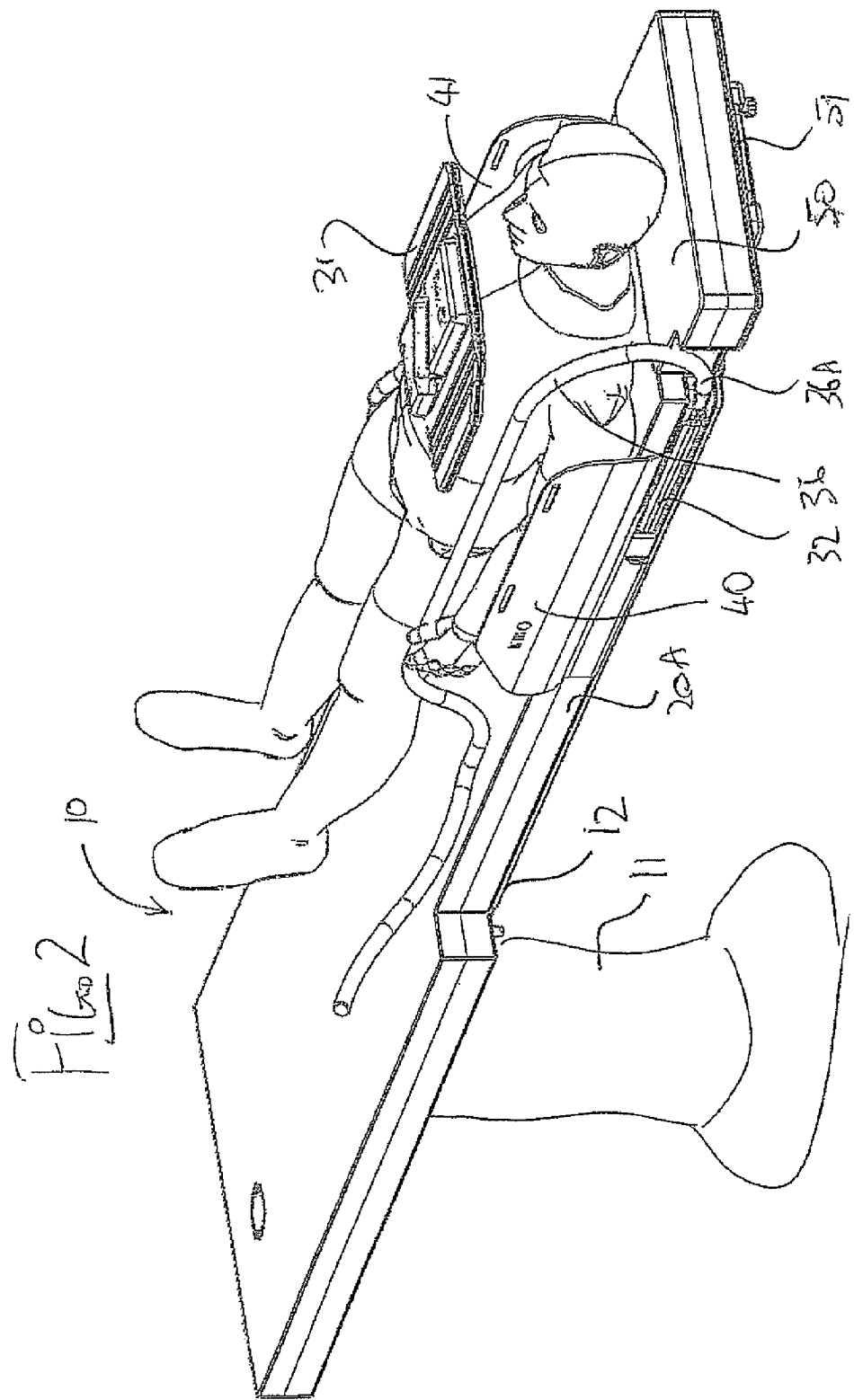
FIG. 2 is an isometric view of a table for mounting the patient, the base being omitted for convenience of illustration, and showing the RF coil construction for imaging of the upper torso of the patient.

In FIG. 1 is shown an arrangement for carrying out Magnetic Resonance Imaging and X-ray imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A. The room contains an X-ray imaging system 4 mounted on rails 5 and includes an X-ray transmitter 6 and receiver 7 mounted on a C-shaped support 8. The X-ray system is of a conventional construction commercially available from a manufacturer such as Siemens. The table 10 described and illustrated herein is used in an arrangement where the patient remains in position on the table while imaging is effected using MRI and X-ray.

Additional unique multi-room layouts, configurations and applications are possible when a rotating MRI system is designed. In this case, the following multi-room configurations are used as examples to illustrate the variety of applications which are possible, with all of these applications being financially beneficial to the healthcare industry.

The magnet system 3 moves into a room within 1 minute, and the doors 2 open within seconds, so the limiting factor on effectiveness of usage of the magnet system is providing the patients into and out of the room, prepping the patients if required, and discussing the imaging with the patients. It is known that a reasonable amount of time per imaging event is 60 minutes, and therefore the movement of the MRI scanner into and out of a room is not the limiting time value. As well, the efficiency of a multi-room system becomes more difficult to schedule as the need for both diagnostic and interventional procedures occurs. The following configurations are now possible:

A three room diagnostic configuration in which the central magnet holding bay 1A houses the magnet and the diagnostic patients are organized in the three rooms including the room 1 and a further room not shown beyond the bay 1A. The doors 2 to room 1 open, the magnet holding bay 1A becomes part of room 1. When the magnet moves to the second room, the magnet may not move but may extend its diagnostic table, the patient lies on the diagnostic table, imaging is performed, no need to do intervention is found, the patient exits the diagnostic table and the magnet moves back into the holding bay, ready for use by one of the other rooms. The magnet then may draw in its table, rotates to the doors for that room, and the process for the other room begins. In this case, the magnet does not move in a translational direction, such as on rails, but simply rotates.

A two room system is in the corner of the hospital. In this case, the magnet both rotates and translates. There is a central magnet holding room, with doors in each of the two 90 degree directions, and the magnet can rotate its diagnostic table in whichever direction is required, or can rotate to allow the opposite end of the magnet to enter the room first. This approach allows existing diagnostic functionality and applications to be used in either room, or allows both rooms to serve as intra-operative rooms without any significant change to magnet controls and monitoring. This two room corner system cannot be done without a rotating magnet.

The system can be suspended from the ceiling or mounted on a floor mounted bearing, with either system providing rotation of the magnet. The MRI system may also be suspended from the ceiling on rails, such that it can also be translated in space using the rail system. The rotational mechanism can either be located between the magnet and the rails, or above the rails. The below track and above track rotators have different properties for different configurations. The below track rotator allows for easiest upgrade of existing sites, whereas the above track rotator works like a roundhouse in a railway yard, in that the rail, MRI system and all associated systems are rotated.

Turning now to the arrangement including the X-ray system which cooperates with the moving magnet described above, the system consists of the movable magnet integrated with an X-ray system such that the patient can be imaged by either modality on the same table. The patient does not move.

The MR is a high-field (e.g. 1.5 T or 3 T) magnet that moves on overhead rails between the two or more rooms as described above. In the system described, one or more of these rooms contains an X-ray system, either a single-plane or a biplane. When the magnet is moved out of the X-ray examination room and a set of RF and X-ray shielded doors is closed, the examination room functions as a conventional X-ray lab and can be used with conventional equipment. In particular, X-ray guided interventions may be performed.

The arrangement may be used in a typical three room configuration with the Angiography Room (AR) on the left, a Diagnostic Room (DR) in the middle, and an Operating Room on the right. The magnet moves on overhead rails between the rooms and can image in each.

When MR imaging is required, the X-ray equipment is safely stowed, the doors open, and the magnet is brought into the room over the patient on the table. The RF shield encompasses the AR so all the equipment in the X-ray examination room is made RF-quiet. MR imaging can then be performed. Afterwards, the magnet is removed from the room, the doors closed, and the X-ray equipment is returned to its working position.

The MR scanner is used to provide information complementary to that obtained using X-ray. It can be used, for example, to perform a baseline assessment prior to intervention as well as to perform a post-intervention assessment. Such an assessment may include perfusion and viability studies of, for example, the heart or of the brain.

As example workflows for the system, consider elective procedures and emergency cases, such as acute stroke or acute coronary syndromes.

In the Elective Procedure Workflow, a preliminary, baseline MR scan can be obtained with the patient either in the diagnostic room or in the angiography room; this is basically a pre-procedure MR scan. The objective is to measure baseline parameters that are clinically relevant. For a cardiac procedure, this may include baseline cardiac function and myocardial viability.

After the MR scan, the patient is transferred to the angiography room if MR imaged in the diagnostic room, or simply remains on the table if already in the Angio room, where coronary or cerebral angiography and angioplasty, followed by stent placement are conducted, if required, in the customary fashion under X-ray fluoroscopy.

The MR Scanner magnet enters the angiography room and acquires the appropriate MR images. After reviewing the MR data and possibly correlating with the X-Ray data, the interventionist can either discharge the patient or continue treatment.

In the emergency Case Workflow, the patient is admitted and undergoes preparation in the Emergency room (both groins shaved, screening for MR examination, metal check, etc.). The patient is brought to AR (in the case of an acute myocardial infarction diagnosed by ECG) and vascular access via the groin is established. MR Imaging could take place in the AR for baseline assessment in order to minimize movement of the acute patient. The scanner is brought into the AR for MR measurement of baseline cardiac function and perfusion imaging in a cardiac case. In the case of stroke, the MR images will reveal if interventional therapy is indicated. In both cases, MR baseline imaging is completed and processed in a minimum time period. In both stroke and cardiac patients angiography and intervention (angioplasty, thrombectomy, or delivery of clot-busting drugs at the site of occlusion) are performed in the customary fashion, under X-Ray fluoroscopy, if so indicated.

The MR Scanner is brought into the AR for subsequent MR images acquisition. After reviewing the MR images and possibly correlation with the X-ray data, the interventionist will discharge the patient or continue with treatment.

In the arrangement for moving the X-ray system as shown in FIG. 1 the MR enters the X-ray examination room and moves over the head end of the table 10. Since the path of the MR passes right through the location of the C-arm stands, the latter must be moved before the magnet may enter. Depending on need, a floor-mounted C-arm stand may be moved on floor rails, floor turntable, or a boom mounted on the floor or wall. Depending on need, a ceiling-mounted C-arm stand may be moved using extended rails to park it at the foot end of the table, by mounting the stand rails on a platform suspended from the movable magnet rails, or by fixing the stand rails on a platform with a telescopic arm to move them laterally.

Using a solution to move a floor-mounted stand together with a mover for a ceiling mounted stand provides a mechanism to move a biplane system. The mover can provide a mounting position of the single plane or biplane at some non-zero angle to the MR rails, e.g., 90 degrees.

A global safety system is generally required for the safe and effective integration of the two modalities. There are a number of hazards in the AR, such as: collision with moving stands, table, and MR; ferrous objects being drawn into magnet bore; and unwanted radiation exposure.

The global safety system is responsible for a number of aspects of the system:

X-ray generation is disabled when the AR/DR doors are not closed.

Motion of the C-arms is disabled when unsafe to do so.

Motion of the table is disabled when unsafe to do so.

Forward travel of the MR is disabled when unsafe to do so.

The direction of magnet travel from the DR towards the patient table is referred to as forward travel, and the opposite direction as reverse travel. The path from the magnet's home position in the DR to its imaging position in the AR is divided into three zones:

Far Zone: the magnet and the C-arms are far enough apart that each may operate independently without safety concern. The patient table may move freely.

Near Zone: the magnet is close enough to the C-arms that the C-arms must be safely parked and not move. The patient table may move vertically, horizontally, and tilt; it must not swivel about its base.

Table Zone: the magnet is over the table, or nearly so. The C-arm stands must be safely parked and not move. The table must be in the correct position for MR imaging and must not move.

In the Near Zone, the C-arm stands must be safely parked and not move. If this is not the case, forward motion of the MR is interrupted, preventing the MR from entering the Near Zone. Similarly, at the transition between the Near and Table Zones the condition that the table must be in the position for MR imaging (i.e. at correct height and lateral position to enter the magnet bore) is checked. If the table is not in the correct position, the magnet may not move forward into the zone.

The ESCP (Equipment Safety Check Point) and PSCP (Patent Safety Check Point) divide the path into three zones; Far, Near, and Table. Interlocks prohibit the magnet from advancing into a zone if it is unsafe to do so.

The safety system controller communicates with the movable magnet controller, the RF door controller, the X-ray equipment and the patient table, as shown in FIG. 1. The signalling includes the following information:

The moveable magnet controller sends the magnet zone and receives a signal indicating whether forward travel is permitted.

The door controller sends a signal indicating whether the door is open or closed.

The X-ray controller sends information on the location of the C-arm stands and table position, and receives signals indicating whether stand motion or table motion is permitted.

The Patient Handling System or support table is shown in FIGS. 2 to 7 as indicated generally at 10. The patient support table includes a base 11 of a conventional construction which allows the base to move a patient support portion 12 to required locations in height and in orientation. Suitable drive mechanisms and couplings are known in the art and thus are not required to be described herein. At the top of the base 12 is mounted the patient support portion in the form of a generally planar body 12 formed of a fiber reinforced plastics material so as to define a surface area sufficient for supporting the patient while lying on the patient support portion. Thus as best shown in FIG. 5, the patient support 12 includes a rear edge 13 at or beyond the feet of the prone patient together with two side edges 14 and 15 spaced by a distance sufficient to receive and contain the legs, body and arms of the patient to be supported by the support portion. At a forward end 16 is provided a forwardly extending narrower portion 17 for underlying the head of the patient. Thus the width through the side edges 14 and 15 is substantially constant up to the edge 16 where the support portion narrows in width generally at a location adjacent the shoulders of the patient to provide a narrower plate portion 17 of sufficient width for generally supporting the head of the patient.

On top of the patient support portion 12 is provided a mattress 18 which is shaped to overlie the patient support portion 12. Thus the mattress has a rear edge 19 which is located at the edge 13 of the portion 12 and two side edges 20 and 21 which are adjacent the side edges 14 and 15. A step portion 22 is provided in the mattress where the mattress increases in width. Thus the sides include side portions 20A and 21A of reduced width which are located at the positions intended to be inserted into the cylindrical bore of an MRI magnet. The wider portions of the mattress beyond the step 22 are generally intended to remain outside the magnet bore so that these portions can be of increased width allowing more stability for the patient. The portion to be inserted into the bore is cantilevered forward from the base 11 so that the whole of the base is located beyond the step 22 within the area of the wider part of the mattress.

The structural support for the patient is provided by the support portion 12 which is formed of a fiber reinforced resin material where the fibers are laid in sheets and infused by the resin material to provide a flat structural member of sufficient strength to carry the weight of the typical patient. In order that the patient support portion be formed of a material which does not interfere with the operation of the magnet or the generation and acquisition of the necessary signals used in magnetic resonance imaging, the fiber reinforcement selected for use in the structure of the portion 12 is a fiber which has sufficient strength to provide the necessary resistance to bending but a fiber which is non-electrically conductive. Thus carbon fibers cannot be used since long carbon fibers generate or allow currents to flow within the structure of the portion and such currents will interfere with the necessary signals. The currents are generated by the high magnetic fields within the magnet and by the electro magnetic signals which are generated within the magnet for use in the magnetic resonance imaging. Typically aramid fibers such as Kevlar™ can be used in replacement for the carbon fibers typically used in such structures.

The mattress is formed of a stiff foam material encased by a skin to provide an exterior surface which is resistant to fluids and can be readily cleaned for sterilization to be used in clinical situations. The mattress extends from a step 22 through to a forward edge 25 located at the end edge 16. The mattress does not include a portion extending beyond the end edge 16 into the area of the plate 17.

The mattress is formed in two layers of formed material to provide a typical thickness of the order of two inches. The second or lower layer of foam is omitted in the area between the end edge 25 and a location 26 to define a receptacle 27 within the mattress at the upper surface of the portion 12. On top of the receptacle is provided a second layer of foam material so that the receptacle is spaced from the body of the patient by a layer of foam, albeit a thinner layer of foam so that the patient is comfortably supported throughout the full length of the patient despite the presence of the receptacle underneath the chest area of the patient.

As shown in FIG. 7, the receptacle 27 can be filled by an insert portion 28 formed of the same foam material with a covering skin. The portion 28 is shaped to fill the receptacle so that it is rectangular with two parallel sides allowing to slide between the edge 25 of the receptacle and the end 26 of the receptacle. The sides of the insert portion 28 carry hook and fastener connection strips 29 which cooperate with similar strips 30 on the edge 26 and on a depending flap 31 at the end 25. In practice the Insert piece 28 can be inserted into place when the patient is removed since the table is to be set up for imaging either the head or the chest of the patient and in the case where the imaging is to be of the head, the chest coil is omitted so that in this case the insert piece 28 is placed onto the support portion 12 and the mattress placed on top of it.

When the imaging is to be of the chest, the anterior chest coil 31 is arranged to be placed on top of the chest of the patient when in place for imaging on the mattress and also the posterior coil 32 is arranged to be inserted into the receptacle 27. In order to protect the coil 32 and in order to ensure that the mattress remains properly flat over the receptacle 27, a flat rectangular sleeve 33 is provided which is inserted in place under the mattress when the coil 32 is to be used. Thus when the table is set up for the imaging of the chest, the insert piece 28 is omitted and in its place the sleeve 33 is inserted. This allows the posterior coil 32 to slide into place through a slot shaped opening 34 in one side of the sleeve 33 at the side of the mattress 18. The coil 32 is shaped to fit simply as a sliding fit into the interior of the sleeve. Thus when it is intended to carry out magnetic resonance imaging, the posterior coil 32 can simply slide into place allowing the patient and the cantilever portion of the table to slide into the magnetic bore to carry out the imaging.

When the imaging is complete and the patient is to be imaged by an X-ray system, the coil 32 can simply be removed by pulling the coil out of the opening 34 of the sleeve 33. The anterior coil 31 can also simply be removed from the top of the patient chest so that all coil portions are removed from the table allowing X-ray imaging to be carried out without any interference from any metal components in the table.

As best shown in FIG. 3, the cable from the coil 32 which transmits the received signals to the control system of the magnetic resonance imaging apparatus is shown at 36 and is arranged on the coil at the forward end of the coil exiting from a front surface 32A of the coil immediately adjacent the side surface 32B of the coil. Thus the cable 36 extends at this position forwardly from the coil 32. The sleeve 33 has a slot 33A located in the front surface 33B of the sleeve adjacent the opening 34. This allows the coil to be inserted through the opening 34 with the cable 36 and its innermost end 36A extending through the slot 33A and thus extending forwardly from the coil and forwardly from the sleeve 33. The cable thus emerges beyond the end 25 of the mattress 18 and no part of the cable extends beyond the side edge 20A of the mattress 18. The cable 36 can thus be laid so that it extends beyond the end 25 whereupon it curves upwardly and rearwardly to form a cable portion 36B passing over the shoulder of the patient and along the body of the patient at a junction between the arm and body of the patient to a position beyond the arm where the cable includes a portion 36C lying over the mattress and particularly the wider part of the mattress beyond the shoulder 22. In this way the cable can be directed so that it is properly controlled and laid in position by the operators prior to the imaging process taking place. The cable is properly managed as it passes over the patient and the cable has no possibility of falling outwardly in an uncontrolled manner from the table. No part of the table projects beyond the sides of the mattress and the support portion 12 so that these can be of the maximum dimension allowable to enter the bore of the magnet.

The table further includes arm engagement members 40 and 41 arranged to contain the arms of the patient to ensure that they are retained on the mattress and cannot fall to the sides as the patient resides on the support during the imaging process. Even though the table remains stationary during the imaging both by the magnetic resonance imaging system and by the x ray system, it is necessary to confine the patient so that the patient cannot move side to side and cannot drop one arm to the side of the table during the imaging process.

The arm engagement members best shown in FIG. 5 include a generally upstanding board 42 which has a length from a rear end 43 to a forward end 44 which is sufficient to extend along substantially the whole of the arm of the patient from the hand to the shoulder. The board is contoured with a generally upstanding portion and an upper portion which is inclined inwardly and upwardly so as to form a slight channel shape better confining the arm of the patient. The board is attached to a mounting plate 45 which is a flat plate with side edges 46 and 47 and an inner edge 48. The plate 45 includes an upturned flange portion 49 standing upwardly from the plate and having a length equal to the length of the plate between the edges 46 and 47. At the top of the flange portion 49 the board 42 is attached as an integral connection but the board extends from the flange 49 forwardly to the forward edge 44. Thus the plate 45 is restricted to a distance so that the front edge 47 is recessed from the front edge 44 of the board. The length of the plate 45 is such that it can be inserted underneath the patient between the mattress and the flat support 12 so that the plate is pinched by the weight of the patient holding the board in place against movement longitudinal or outward to the side. The length of the mounting plate 45 however, is restricted so that it terminates at a position just beyond the edge 26 of the mattress so that the plate does not extend under the sleeve 33 or into the area of the coil 32. Thus the arm support board 42 is cantilevered forwardly from this plate and the plate itself does not enter into the area of the imaging defined by the coil. Of course the coil is located at the required position for the part of the patient in the chest to be properly imaged both in the magnetic resonance imaging system and in the x-ray system.

When the coil 32 is removed, the arm boards remain in place so that the patient can remain lying in place on the mattress and the patient remains confined by the arm engagement members 40 and 41 as the magnet is removed and the x-ray system is moved into place. The X-ray process can therefore take place and therefore the boards hold the patient in place while the mounting plates 45 are located at a position which does not interfere with the x-ray process. As shown in FIGS. 3 and 5, during X-ray imaging of the chest the head of the patient is simply supported on a mattress extension portion 50 which is carried on a plate portion 51. This plate portion has a width slightly less than the width of the support portion 12. Thus the plate portion 51 includes a rear edge 51A and a parallel front edge 51B. The plate portion also includes one side edge 51C on the side opposite the cable 36. At the cable 36, the plate provides a side edge 51D which includes a recess 51E into which the cable 36 is inserted. The mattress portion 50 also includes a rear edge 50A coincident with the edge 51A. The mattress portion 50 also includes a front edge 50B coincident with the edge 51B and side edges 50C and 50D coincident with the side edges 51C and 51D. Again therefore the mattress portion includes a recess 50E into which the cable is inserted. The plate 51 is carried on a pair of guides 52 and 53 which form a slot for sliding over the plate portion 17 at the side edges thereof. Thus the plate 51 slides over the top of the plate portion 17 and is held in place by the slot guides on the underside together with a screw clamp 54 which pinches the edge of the plate portion 17 to ensure that the support plate 51 remains in place at the end of the mattress. The mattress portion 50 is then placed on top of the plate portion 51. The mattress 18 and the mattress portion 50 are conveniently held in place by hook and loop fastener strips 56 located at suitable locations on the parts of the support 12 on which they are mounted. The mattress is thus properly held in place allowing the patient to be moved on top of the mattress without the danger of the mattress sliding to one side. Thus as shown in FIG. 3, when the imaging is carried out at the chest area, the heads of the patient simply rests upon the mattress portion 50 which may be supplemented by a cushion or other comfort receptacle as required.

Turning now to FIGS. 6 and 7, the table is shown in these figures configured for imaging of the head. During the imaging of the head, the chest coils are of course fully removed. In addition the plate 51 and the mattress portion 50 are also removed allowing a more effective and accurate supporting of the head for imaging of the head. Thus there is provided a head support generally indicated at 70 and a head coil 71 including an anterior portion 72 and a posterior portion 73. The head support 70 comprises a channel member 74 which is shaped to receive the rear of the head of the patient and hold this supported at all times during the imaging process. The head support 74 comprises a simple channel or it can comprise a flexible receptacle portion with strapping to hold the head more effectively in place. Either type of head support is mounted on a bracket 75 carried on a slot shaped mounting member 76 with bottom slot portions 77 and 78 which engage onto the edges of the plate 17 in the same manner as previously described in respect of the plate 51. Thus the slot shaped mounting member 76 slides into place and can be fastened in place by a fastening screw 79. When in place, a front edge 80 of the mounting 76 butts against the edge 16 of the support 12 at the bottom of the plate portion 17. The channel member 74 is thus cantilevered forwardly from the mounting brackets 75 to a front edge 82 spaced forwardly of the bracket and forwardly of the edge 16 to a position overlying the plate 17 but spaced upwardly from the plate 17.

The posterior coil portion 73 includes a curved upper surface 73A which follows approximately the outer surface of the channel member 74 so that it can pass over the underside of the channel member 74 in a sliding action longitudinally of the head of the patient.

It will be appreciated that the shapes of the surface 73A and the bottom surface of the channel 74 need not be closely accurate provided the shapes provides sufficient clearance to allow sliding action to occur. However it is preferred that the coil be as close as possible to the rear of the head of the patient so that the channel member 74 is formed of a thin material sufficiently strong to support the weight of the head and the surface 73A is closely adjacent the rear surface of the support channel 74.

The posterior coil 73 is carried on a support bracket 85 which also includes a slot shape mounting 86 for sliding onto the plate portion 17 at a position beyond the mounting 75 and its slot shaped mounting portion 77. As best shown in FIG. 6, therefore, the head support channel 74 is located inside the posterior coil 73 and the mounting brackets 75 and 85 are arranged so that they both fit onto the plate 17 with the mounting bracket 85 in front of the bracket 75. Thus the bracket 75 can remain in place and the support 73 can hold the head of the patient while the posterior coil portion is moved into place or is removed from place.

The anterior coil portion is mounted on the posterior coil portion so it can slide into place as a common structure or it can be removed and placed onto the posterior coil portion when the posterior coil portion is already installed.

As shown in FIG. 7, there is a sliding interconnection between the rear surface of the posterior coil 73 and the top of the bracket 85 allowing the posterior coil to be removed from the bracket.

The patient handling system thus contains the following key components: the patient table 11, the head holder 73, and MR imaging coils. The system, including integration of the key components, is specially designed to permit imaging with both MRI and X-ray imaging modalities, while maintaining sufficient image quality and workflow.

The patient table is designed to allow the patient to be scanned with both MR and X-ray imaging modalities. The patient table is comprised of two major components: the table pedestal and the tabletop. The tabletop is fully MR and X-ray compatible; the table pedestal does not adversely impact image quality during MR scanning (i.e. does not impact homogeneity of magnetic field), the pedestal also does not experience significant forces from the magnetic field. The tabletop is positioned so that the table pedestal (which is also not X-ray compatible) is at a distance that is sufficiently away from the imaging site. The tabletop integrates the head holder, arm boards and MR imaging coils.

The head holder supports the patient's head during the procedure and must also be MR and X-ray compatible. The head holder integrates into the patient table in a manner that is very efficient to position and remove. The MR imaging head coils may also be integrated with the head holder and are easily positioned and removed at the imaging site.

The MR imaging coils consist of head coils (for imaging the head and upper spine), as well as coils for imaging other areas of the body (e.g. cardiac coils for imaging chest). MR coils are not X-ray compatible and thus are positioned and removed from the imaging area when switching between imaging modalities without having to move or interfere with the patient. An example is the MR coils used for cardiac imaging, which consist of an anterior (placed on top of the patient's chest) and the posterior coil (placed underneath the patient's back). The anterior coil can simply rest on the patient; the posterior coil is integrated into the tabletop in a variety of options: underneath the tabletop, within the structure of the tabletop, or on top of the tabletop, which also includes integrating the posterior coil into the tabletop mattress. All of these methods are designed such that the coils are easily and efficiently positioned and then removed from the imaging area.

During certain medical procedures, both X-ray and MR imaging modalities may be employed, at separate times during the procedure. Since MRI coils are not X-ray compatible, it is necessary to position and remove the coils quickly and easily when switching between MRI and X-ray imaging. For cases where it is necessary to keep the patient in a fixed position during the procedure, the imaging coils must also be positioned and removed without moving or shifting the patient in any way. For example, cranial procedures will employ the head holder to secure the head of the patient during the entire procedure. The MR imaging head coils will be easily positioned around the head holder without moving the head holder or the patient's head in any way. A second example is procedures requiring chest/abdominal imaging. The anterior coil may be positioned on top of the patient; the posterior coil is positioned into a slot or cavity in the table top mattress, the tabletop itself, or below the tabletop. All methods of positioning the posterior coil maintain a constant position for the patient.

The patient table consists of a table top that is completely MR and X-ray compatible. The tabletop also enables the integration of various MR imaging coils, such as head coils and cardiac coils, with the special feature of positioning and removing the coils without moving or shifting the patient in any way. Coil integration can involve a slot or cavity within the tabletop itself or within the tabletop mattress. Alternatively, the coils can also be positioned underneath the table, through a mounting bracket or shelf component.

A special cavity insert device is also included to fill the void in the tabletop or mattress when the MR imaging coil is not in place; this provides additional structural strength.

There is provided reinforcing material around the coil cavity in the table/mattress to provide for extra rigidity when switching between the imaging coils and the cavity insert. Alternatively, the cavity may be lined with an inflatable pocket that upon inflation lifts the patient enough to easily insert and remove the coil to replace with cavity insert. The tabletop also includes a means of easily positioning and removing the head holder; this includes a ridge or ledge around the head end of the tabletop, where the head holder may slide on with a dovetail interface. The imaging head coils also are integrated to the table in this fashion.

The head holder and table adapter assembly include the head holder that secures the head during the procedure and also a table adapter that secures the head holder to the patient table and also provides a means of adjusting the position/orientation of the head holder. The entire assembly is completely MR and X-ray compatible. There are various means of securing the patient's head, including a horseshoe head holder, a sling/suspender head holder, and a head cradle. The horseshoe head holder includes a rigid frame that is cushioned by gel, foam, or air inflated pillows; the sides and top of the patient's head may be supported by a strap or by side cushions. The frame may also be adjustable for accommodating a large range in head sizes. The sling/suspender head holder consists of soft material (e.g. fabric) that is shaped into a sling to support the back and sides of the head. The top of the head may be supported by a fabric strap; foam padding may insert between layers of material in the sides of the sling to cushion the head where the table adapter interfaces to the sling/suspender head holder. The head cradle is a scoop-shaped device that cradles the head and neck of the patient and includes foam or inflatable air pillows to cushion the back of the patient's head (for comfort) and also preventing the patient from moving the head from side to side. One additional feature of the inflatable pillow is that the pillow may be deflated to bring the head down slightly so that it is even closer to the portion of MR imaging head coil that is positioned directly underneath the head of the patient, which will increase MR image quality. The table adapter may interface to the head holder at various orientations, such as at the front of the head holder (closest to the patient's head), at the back of the head holder (furthest from patient table), along the sides of the head holder, or along the top of the head holder.

The invention claimed is:

1. Apparatus for use in Magnetic Resonance imaging of a part of a patient comprising:
   patient support table;
   an RF coil for use in the MR imaging of the upper torso of the patient including a posterior coil portion for location underneath the upper torso;
   the patient support table comprising a table support base for mounting in fixed position in an imaging suite;
   the patient support table comprising an upper patient support portion for structurally supporting the patient with the part of the patient exposed for imaging;
   the upper patient support portion of the patient support table being cantilevered from the table support base in a longitudinal direction so as to extend into a bore of an MRI magnet from one end of the magnet to an imaging zone of the magnet;
   the upper patient support portion having a bottom surface and a substantially planar upper surface;
   a mattress applied over the substantially planar upper surface of the patient support portion, the mattress having an upper surface for contacting the patient;
   a receptacle defined in one or both of the upper patient support portion and the mattress for receiving the posterior coil portion;
   the receptacle being located underneath the upper surface of the mattress and above the bottom surface of the upper patient support portion such that the posterior coil is supported from below by at least a part of the upper patient support portion;
   the receptacle having an inlet opening located and arranged such that, with the mattress in place on the support portion and the patient in place on the mattress, the opening is exposed beneath the upper surface.

2. The apparatus according to claim 1 wherein the receptacle is provided in the mattress.

3. The apparatus according to claim 2 wherein there is provided a stiffener sleeve for location in the receptacle in the mattress into which sleeve the posterior coil portion is inserted, the stiffener sleeve providing support for the patient with the posterior coil portion removed.

4. The apparatus according to claim 2 wherein there is provided a replacement insert portion for insertion into the receptacle in the mattress when the posterior coil portion is not used.

5. The apparatus according to claim 2 wherein the receptacle extends substantially across the full width of the mattress.

6. The apparatus according to claim 2 wherein the receptacle extends partly through the thickness of the mattress with a portion of the thickness of the mattress above the receptacle.

7. The apparatus according to claim 2 wherein the receptacle is located at a forward end of the mattress.

8. The apparatus according to claim 1 wherein the opening is in an edge such that the coil is inserted into the receptacle through the opening by movement in a horizontal direction.

9. The apparatus according to claim 1 wherein the opening is in one side edge.

10. The apparatus according to claim 1 including a pair of arm engagement members each arranged on a respective side of the patient support portion for engaging and retaining a respective one of the arms of the patient on the mattress while the patient lies prone on the mattress;
    each arm engagement member comprising an elongate plate portion arranged to extend along the side of the mattress and to stand upwardly therefrom to hold the arm of the patient inwardly with a rearward most edge adjacent the hand of the patient and a forwardmost edge adjacent the shoulder of the patient;
    each arm engagement member comprising a mounting plate connected to the elongate plate portion and arranged to extend generally at right angles to the elongate plate portion between the mattress and the patient support portion of the table for holding the arm engagement position in place at the side of the patient support portion of the table;
    wherein the mounting plate has a forwardmost edge spaced rearwardly from the forwardmost edge of the elongate plate portion and located such that the mounting plate is wholly located on the patient support portion of the table at a position spaced from the upper torso of the patient and such that the posterior coil portion can be inserted into the receptacle in front of the mounting plate.

11. Apparatus for use in magnetic resonance imaging of a part of a patient comprising:
    a patient support table;
    an RF coil for use in the MR imaging including a posterior coil portion for location underneath the patient;
    the patient support table comprising a table support base for mounting in fixed position in an imaging suite;
    the patient support table comprising and an upper patient support portion for structurally supporting the patient with the part of the patient exposed for imaging;
    the upper patient support portion of the patient support table being cantilevered from the table support base in a direction longitudinal of the axis so as to extend into a bore of an MRI magnet from one end of the magnet to an imaging zone of the magnet;
    a mattress applied over the patient support portion;
    a pair of arm engagement members each arranged on a respective side of the patient support portion for engaging and retaining a respective one of the arms of the patient on the mattress while the patient lies prone on the mattress;
    each arm engagement member comprising an elongate plate portion arranged to extend along the side of the mattress and to stand upwardly therefrom to hold the arm of the patient inwardly with a rearward most edge adjacent the hand of the patient and a forwardmost edge adjacent the shoulder of the patient;
    each arm engagement member comprising a mounting plate connected to the elongate plate portion and arranged to extend generally at right angles to the elongate plate portion between the mattress and the patient support portion of the table for holding the arm engagement position in place at the side of the patient support portion of the table;
    wherein the mounting plate has a forwardmost edge spaced rearwardly from the forwardmost edge of the elongate plate portion and located such that the mounting plate is wholly located on the patient support portion of the table at a position spaced from the upper torso of the patient.

12. The apparatus according to claim 11 wherein the mounting plate is connected to a vertical portion connected thereto and extending upwardly to the elongate plate portion to hold the elongate plate portion at a raised position from the mounting plate, the vertical portion having a forwardmost edge coterminous with the mounting plate.

13. The apparatus according to claim 11 wherein there is provided a receptacle in one or both of the patient support portion and the mattress for receiving a posterior coil portion of an RF coil for location underneath the patient for use in the MR imaging and wherein the mounting plate is arranged such that the forwardmost edge thereof is spaced in the rearward direction from the receptacle.

14. The apparatus according to claim 13 wherein the receptacle is provided in the mattress.

15. The apparatus according to claim 14 wherein an opening into the receptacle is in one side edge of the mattress such that the coil is inserted into the receptacle through the opening by movement in a horizontal direction.

16. Apparatus for use in Magnetic Resonance imaging of a part of a patient comprising:
    patient support table;
    an RF coil for use in the MR imaging including a posterior coil portion for location underneath the patient;
    the patient support table comprising a table support base for mounting in fixed position in an imaging suite;
    the patient support table comprising an upper patient support portion for structurally supporting the patient with the part of the patient exposed for imaging;
    the upper patient support portion of the patient support table being cantilevered from the table support base in a longitudinal direction so as to extend into a bore of an MRI magnet from one end of the magnet to an imaging zone of the magnet;
    a mattress applied over the patient support portion and having an upper support surface for supporting the patient;
    the mattress having one side edge of the mattress arranged along one side edge of the patient support portion;
    the posterior coil portion being located underneath the upper support surface the mattress;
    the posterior coil portion including a cable for communication of RF signals from the posterior coil portion to a control system for controlling the magnetic resonance imaging with the cable being located at said one side edge;
    the cable being connected to the posterior coil portion adjacent said one side edge of the mattress;
    said one side edge of the mattress having a recess portion located such that the cable emerges from the posterior coil portion at said recess portion at said one side edge of the mattress and passes from the posterior coil portion over the mattress without projecting outwardly beyond said one side edge of the upper patient support portion.

17. The apparatus according to claim 16 wherein the cable is connected to the posterior coil portion at a forward end thereof and is arranged such that the cable emerges from the posterior coil portion at a forwardmost edge of the mattress immediately adjacent said one side edge.

18. Apparatus for use in Magnetic Resonance imaging of a part of a patient comprising:
- patient support table;
- an RF coil for use in the MR imaging of the upper torso of the patient including a posterior coil portion for location underneath the upper torso;
- the patient support table comprising a table support base for mounting in fixed position in an imaging suite;
- the patient support table comprising an upper patient support portion for structurally supporting the patient with the part of the patient exposed for imaging;
- the upper patient support portion of the patient support table being cantilevered from the table support base in a longitudinal direction so as to extend into a bore of an MRI magnet from one end of the magnet to an imaging zone of the magnet;
- a mattress applied over an upper surface of the upper patient support portion, the mattress having an upper surface for contacting the patient;
- a receptacle defined in the mattress underneath the upper surface of the mattress and above the upper surface of the upper patient support portion for receiving the posterior coil portion;
- the receptacle having an inlet opening located at one edge of the mattress and arranged such that, with the mattress in place on the support portion and the patient in place on the mattress, the opening is exposed for insertion and removal of the posterior coif portion.

19. The apparatus according to claim 18 wherein the receptacle extends substantially across the full width of the mattress.

20. The apparatus according to claim 18 wherein the receptacle extends partly through the thickness of the mattress with a portion of the thickness of the mattress above the receptacle.

21. The apparatus according to claim 18 wherein the receptacle is located at a forward end of the mattress.

22. The apparatus according to claim 18 wherein the opening is in an edge such that the coil is inserted into the receptacle through the opening by movement in a horizontal direction.

23. The apparatus according to claim 18 wherein the opening is in one side edge.

24. The apparatus according to claim 18 wherein there is provided a stiffener sleeve for location in the receptacle in the mattress into which sleeve the posterior coif portion is inserted, the stiffener sleeve providing support for the patient with the posterior coil portion removed.

25. The apparatus according to claim 18 wherein there is provided a replacement insert portion for insertion into the receptacle in the mattress when the posterior coil portion is not used.

* * * * *